United States Patent
Willis et al.

(10) Patent No.: US 9,808,354 B2
(45) Date of Patent: Nov. 7, 2017

(54) IMPLANT INSERTION TOOL

(71) Applicant: Stryker European Holdings I, LLC, Kalamazoo, MI (US)

(72) Inventors: Steven Willis, Mahwah, NJ (US); Zoya Royt, Fresh Meadows, NY (US)

(73) Assignee: Stryker European Holdings I, LLC, Kalamazoo, MI (US)

( * ) Notice: Subject to any disclaimer, the term of this patent is extended or adjusted under 35 U.S.C. 154(b) by 198 days.

(21) Appl. No.: 14/596,688

(22) Filed: Jan. 14, 2015

(65) Prior Publication Data

US 2015/0202053 A1  Jul. 23, 2015

Related U.S. Application Data

(60) Provisional application No. 61/928,625, filed on Jan. 17, 2014.

(51) Int. Cl.
*A61F 2/46* (2006.01)
*A61F 2/44* (2006.01)
*A61B 17/88* (2006.01)
*A61F 2/30* (2006.01)

(52) U.S. Cl.
CPC ........ *A61F 2/4611* (2013.01); *A61B 17/8858* (2013.01); *A61F 2/44* (2013.01); *A61B 17/885* (2013.01); *A61B 17/8872* (2013.01); *A61F 2/4465* (2013.01); *A61F 2002/30523* (2013.01); *A61F 2002/30537* (2013.01); *A61F 2002/30601* (2013.01); *A61F 2002/4627* (2013.01); *A61F 2002/4629* (2013.01)

(58) Field of Classification Search
CPC ............ A61F 2/4611; A61F 2002/4629; A61F 2002/4627; A61B 17/885; A61B 17/8872
See application file for complete search history.

(56) References Cited

U.S. PATENT DOCUMENTS

| 5,453,454 A | 9/1995 | Alicke et al. |
| 5,702,453 A | 12/1997 | Rabbe et al. |
| 5,776,198 A | 7/1998 | Rabbe et al. |
| 6,015,436 A | 1/2000 | Schonhoffer |
| 6,086,613 A | 7/2000 | Camino et al. |
| 6,190,414 B1 | 2/2001 | Young et al. |
| 6,214,050 B1 | 4/2001 | Huene |
| 6,296,665 B1 | 10/2001 | Strnad et al. |

(Continued)

FOREIGN PATENT DOCUMENTS

| DE | 3729600 A1 | 3/1989 |
| DE | 10127924 C1 | 12/2002 |

(Continued)

OTHER PUBLICATIONS

Extended European Search Report for Application No. 15151241.5 dated May 26, 2015.

*Primary Examiner* — Ellen C Hammond
(74) *Attorney, Agent, or Firm* — Lerner, David, Littenberg, Krumholz & Mentlik LLP (57) ABSTRACT

A tool for inserting a spinal implant is disclosed. The tool includes a tube with a handle end, an inserter end having an opening, and a curved portion located between the handle end and the inserter end. A driveshaft with an actuator extends within the tube so that the actuator is proximate to the opening. A knob is attached to the handle end and the driveshaft, wherein turning the knob rotates the actuator. Methods of utilizing the tool, as well as variations of the tool are also disclosed.

13 Claims, 10 Drawing Sheets

(56) References Cited

U.S. PATENT DOCUMENTS

| | | |
|---|---|---|
| 6,344,057 B1 | 2/2002 | Rabbe et al. |
| 6,520,991 B2 | 2/2003 | Huene |
| 6,524,341 B2 | 2/2003 | Lang et al. |
| 6,730,088 B2 | 5/2004 | Yeh |
| 6,752,832 B2 | 6/2004 | Neumann |
| 6,776,798 B2 | 8/2004 | Camino et al. |
| 6,866,682 B1 | 3/2005 | An et al. |
| 7,335,207 B1 | 2/2008 | Smith |
| 7,549,995 B2 | 6/2009 | Schultz |
| 7,575,601 B2 | 8/2009 | Dickson |
| 7,588,573 B2 | 9/2009 | Berry |
| 7,641,693 B2 | 1/2010 | Gutlin et al. |
| 7,648,529 B2 | 1/2010 | An et al. |
| 7,674,296 B2 | 3/2010 | Rhoda et al. |
| 7,691,147 B2 | 4/2010 | Gutlin et al. |
| 7,758,648 B2 | 7/2010 | Castleman et al. |
| 7,811,327 B2 | 10/2010 | Hansell et al. |
| 7,819,920 B2 | 10/2010 | Assaker |
| 7,879,096 B2 | 2/2011 | Dickson et al. |
| 7,909,870 B2 | 3/2011 | Kraus |
| 7,914,581 B2 | 3/2011 | Dickson et al. |
| 7,981,157 B2 | 7/2011 | Castleman et al. |
| 7,988,695 B2 | 8/2011 | Dye |
| 8,114,088 B2 | 2/2012 | Miller |
| 8,123,757 B2 | 2/2012 | Zalenski et al. |
| 8,142,435 B2 | 3/2012 | Refai et al. |
| 8,142,441 B2 | 3/2012 | Refai et al. |
| 8,152,852 B2 | 4/2012 | Biyani |
| 8,157,864 B2 | 4/2012 | Rogeau et al. |
| 8,182,537 B2 | 5/2012 | Refai et al. |
| 8,231,681 B2 | 7/2012 | Castleman et al. |
| 8,241,294 B2 | 8/2012 | Sommerich et al. |
| 8,241,363 B2 | 8/2012 | Sommerich et al. |
| 8,267,998 B2 | 9/2012 | Kraus |
| 8,268,004 B2 | 9/2012 | Castleman et al. |
| 8,282,683 B2 | 10/2012 | McLaughlin et al. |
| 8,328,871 B2 | 12/2012 | Capote et al. |
| 8,337,559 B2 | 12/2012 | Hansell et al. |
| 8,353,961 B2 | 1/2013 | McClintock et al. |
| 8,366,779 B2 | 2/2013 | Dickson et al. |
| 8,377,140 B2 | 2/2013 | DeFalco et al. |
| 8,425,528 B2 | 4/2013 | Berry et al. |
| 8,540,770 B2 | 9/2013 | Woodburn, Sr. et al. |
| 8,568,482 B2 | 10/2013 | Kraus et al. |
| 8,591,585 B2 | 11/2013 | McLaughlin et al. |
| 2004/0210312 A1 | 10/2004 | Neumann |
| 2007/0250171 A1 | 10/2007 | Bonin |
| 2008/0071376 A1 | 3/2008 | Kohm et al. |
| 2008/0167720 A1 | 7/2008 | Melkent |
| 2010/0179655 A1 | 7/2010 | Hansell et al. |
| 2011/0087328 A1 | 4/2011 | Dickson et al. |
| 2011/0251692 A1 | 10/2011 | McLaughlin et al. |
| 2012/0029635 A1 | 2/2012 | Schoenhoeffer et al. |
| 2012/0232659 A1 | 9/2012 | Himmelberger et al. |
| 2012/0232660 A1 | 9/2012 | Davenport |
| 2012/0330426 A1 | 12/2012 | McLaughlin et al. |
| 2013/0006359 A1 | 1/2013 | Fedorov et al. |
| 2013/0066429 A1 | 3/2013 | Capote et al. |
| 2013/0131807 A1 | 5/2013 | MccClintock et al. |

FOREIGN PATENT DOCUMENTS

| | | |
|---|---|---|
| EP | 1219266 A1 | 7/2002 |
| JP | 2261446 | 10/1990 |
| WO | 2004100837 A1 | 11/2004 |
| WO | 2013025448 A1 | 2/2013 |

IMPLANT INSERTION TOOL

CROSS-REFERENCE TO RELATED APPLICATION

The present application claims the benefit of the filing date of U.S. Provisional Patent Application No. 61/928,625, filed Jan. 17, 2014, the disclosure of which is hereby incorporated herein by reference.

BACKGROUND OF THE INVENTION

The present invention relates to an implant insertion tool; more specifically, to an improved insertion tool for use with an expandable spinal implant.

Over time, because of damage or disease, it may become necessary to remove an unhealthy bone structure, such as a part of the spine. For example, an intervertebral disc may herniate, rupture, or collapse; thus requiring a discectomy procedure, which involves surgical removal of a portion or the entire disc. Alternatively, a spinal disease or trauma may impact more than one disc space; thus requiring a corpectomy procedure, which involves removal of a vertebral body and discs. In either instance, once the unhealthy part is removed, an implant is required to restore and maintain bodily function.

One such implant is an expandable implant. These implants include a portion or portions that are capable of moving with respect to one another so as to allow for an increase in the overall height of the implant. The benefit of such an implant is that it can be implanted while exhibiting a lower profile and thereafter be expanded in situ. Expandable implants can be employed in either instance discussed above.

The implantation and expansion of an expandable implant is often affected by the surgical approach and/or patient anatomy. For instance, with respect to spinal implants, a traditional posterior approach requires spinal cord avoidance, often requiring a more oblique approach. Likewise, the overall size of an expandable implant may prevent insertion in a certain orientation (e.g., the implant may be too large in height to fit horizontally through an approach path). In many procedures involving expandable implants, multiple tools are required to facilitate implantation and expansion. It would be desirable to simplify such tooling, while at the same time providing for some added functionality.

Therefore, a need exists for an improved implant insertion tool that can better enable the implantation and expansion of an expandable implant within the body, and particularly within the spine.

SUMMARY OF THE INVENTION

An aspect of the present invention provides an insertion tool with at least one driveshaft. For example, such a tool may comprise a tube with a handle end and an inserter end. In this example, the driveshaft preferably has a first actuator for engaging an implant adjacent to the inserter end. Desirably, the driveshaft may extend within the tube so that the first actuator is proximate to the opening. To engage the implant, a knob is preferably attached to the handle end and the driveshaft so that turning the knob also rotates the first actuator. As another example, the driveshaft may be hollow and a connecting shaft may extend within the hollow driveshaft from the handle end to the inserter end. The connecting shaft may have a second actuator, which may extend within the driveshaft until it is proximate to the first actuator.

The implant insertion tool may also have a first longitudinal axis on a first side of the curved portion and a second longitudinal axis transverse with the first longitudinal axis on a second side of the curved portion. Alternatively, the curved portion may be angular, segmented, or any combination thereof. Aspects of the driveshaft and connecting shaft may also be configured to accommodate this structure. For example, the driveshaft may include a first rigid portion and a second rigid portion; wherein, the first and second rigid portions are joined by a linkage in the curved portion. As another example, the connecting shaft may extend continuously through the curved portion until the second actuator is proximate to the first actuator.

Another aspect of the present invention includes the operation of an implant insertion tool in accordance with the present invention. For example, the exemplary knob disclosed in this application may comprise a first knob associated with the driveshaft and a second knob associated with the connecting shaft. The first knob might be turnably attached to the handle end and rigidly attached to the driveshaft, while the second knob is turnably attached to the handle end and rigidly attached to the connecting shaft. In accordance with this example, turning either the first or second knob preferably operates the respective first or second actuator. As a second example, the first actuator may include a plurality of nubs while the second actuator includes a threaded tip, either of which may be operated by turning the respective first or second knobs.

Desirably, the tube may have a first longitudinal axis and the inserter end may have a second longitudinal axis transverse with the first longitudinal axis. This exemplary configuration may advantageously enable the turning of either the first or second knob to translate a rotational force non-linearly to the respective first or second actuator. To facilitate this mode of operation, the connecting shaft may be flexible while the driveshaft is rigid. In this second example, the inserter end may also have a curved portion with a linkage for engaging an elongated portion of the driveshaft with the first actuator proximate to the open end.

The above disclosed aspects of the present invention may also be incorporated into a system comprising an expandable implant engageable with an implant insertion tool. Alternatively, these aspects may be utilized within a method for implanting an implant within a body. For example, a method in accordance with these aspects may comprise the step of rotating the connecting shaft to engage an implant with the second actuator. Once so engaged, the implant is preferably inserted into the body and then adjusted about a dimension by rotating the first actuator. The driveshaft and first actuator employed may be transverse to each other. Alternatively, the tool may have a curved portion for insertion of the implant into a spine from a posterior approach without contacting the spinal cord. A final aspect of this method may include rotating the connecting shaft to disengage the first actuator from the insertion tool.

Aspects of the present invention may also enable construction of an alternate implant insertion tool by varying the position of the driveshaft with respect to the tube. For example, an alternate tool might similarly comprise a tube extending along a longitudinal axis with a handle end and an inserter end opposite the handle end. Likewise, this tool may also have a driveshaft with a first actuator, connecting shaft with a second actuator, and a first and second knob. In contrast to above, however, an exemplary driveshaft according to these aspects may extend over the tube so that the first actuator is proximate to an open end of the inserter end. In which case, the connecting shaft may extend within the tube and the driveshaft so that the second actuator is proximate to the first actuator.

Additional aspects regarding the operation of this alternative tool are also disclosed. For example, the first knob may be integral with the driveshaft while the second knob is turnably attached to the handle end and rigidly attached to the connecting shaft. In accordance with this example, turning either the first or second knob may rotate the respective first or second actuator. As another example, the connecting shaft may have a joint proximate to the open end for bending the connecting shaft relative to the driveshaft. As yet another example, a slidelock may be slidably mounted to the driveshaft for locking the connecting shaft in a bent position. Alternatively still, the driveshaft may be operatively attached to a release on the tube, the release being configured to prevent the driveshaft from moving without actuation thereof.

Similar to above, any combination of these aspects of may also be incorporated into a system comprising an implant attached to a tool, or included within a method for utilizing the tool to insert an implant into a body. For example, a method in accordance with the present invention may include the initial step of engaging an implant with an insertion tool by rotating a second actuator of the tool in a first direction; wherein, the implant preferably has a bore for receiving the second actuator. Because of the rotatable tip disclosed above, aspects of the method may also include bending a joint attached to the second actuator to rotate the cranial-caudal axis of the implant until it is substantially parallel with a longitudinal axis of the insertion tool.

Likewise, because of the slidelock, aspects of the method may also include locking the joint in a bent position by advancing a slidelock in a first direction, preferably before inserting the implant into a body using the insertion tool. Yet another aspect of the invention may include unlocking the joint so that the implant freely returns to its unrotated position by advancing the slidelock in a second direction opposite the first direction. By advancing the slidelock, the first actuator preferably becomes engageable with the implant so that rotation of the first knob a dimension of the implant. Still yet another aspect of the method may further include rotating the second actuator to disengage the implant. Alternatively, the insertion tool utilized in this method may also have a curved portion for insertion of the implant into a spine from a posterior approach without contacting the spinal cord.

DETAILED DESCRIPTION

The present invention is directed to different embodiments of an implant insertion tool. Although the embodiments depicted in FIGS. 1-10 are designed for use with expandable implants disclosed in connection with the tool are in the form of corpectomy cages, it should be understood that the various embodiments disclosed in this application may be utilized with other types of implants. For instance, the present insertion tool might be modified for use with implants other than those shown, which are designed for placement in a single, natural disc space.

Figure 1:
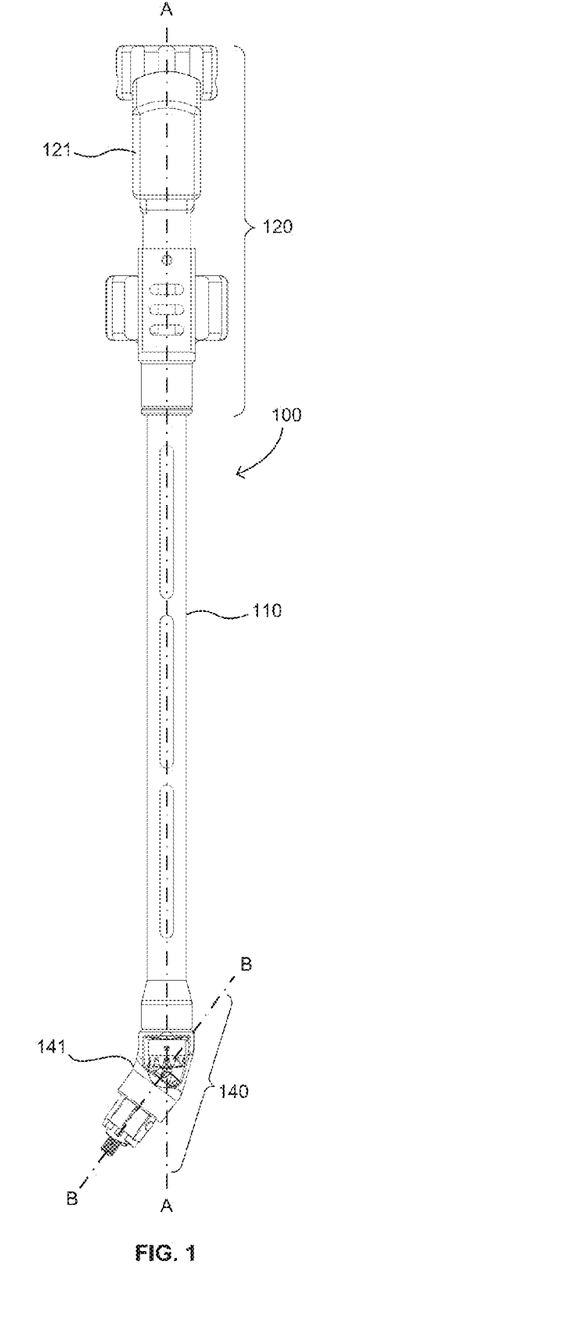
FIG. 1 is a top view of one embodiment of an insertion tool in accordance with the present invention.
Figure 3:
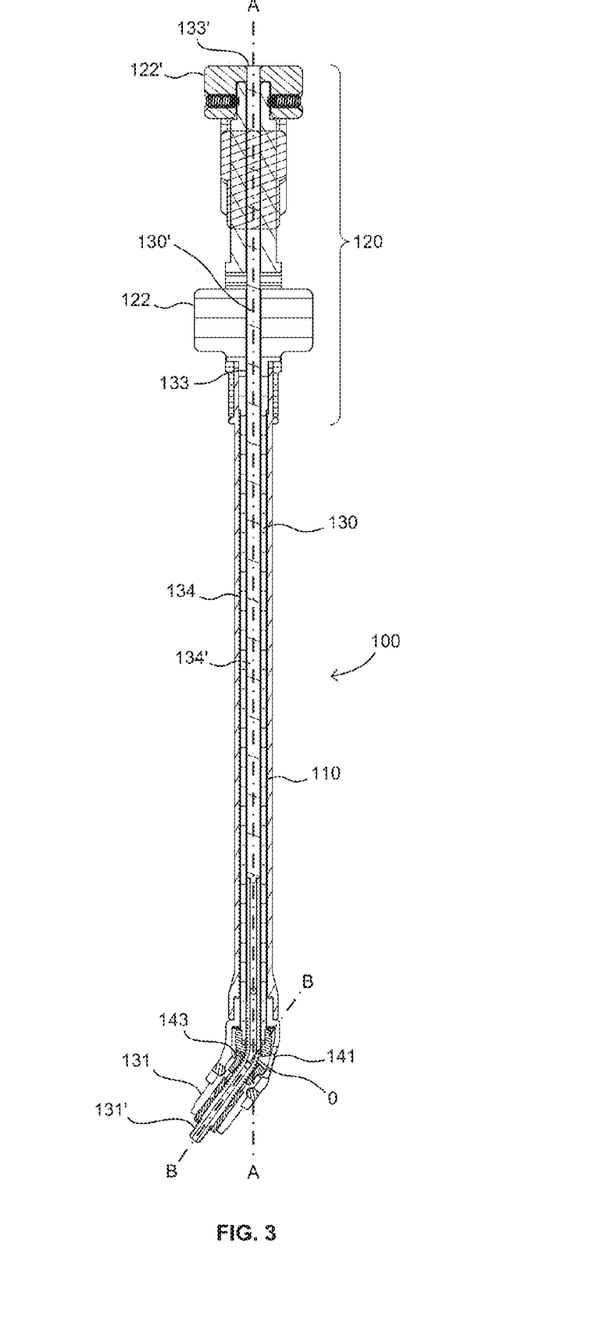
FIG. 3 is a cross-sectional view of the insertion tool shown in FIG. 1.
Figure 4:
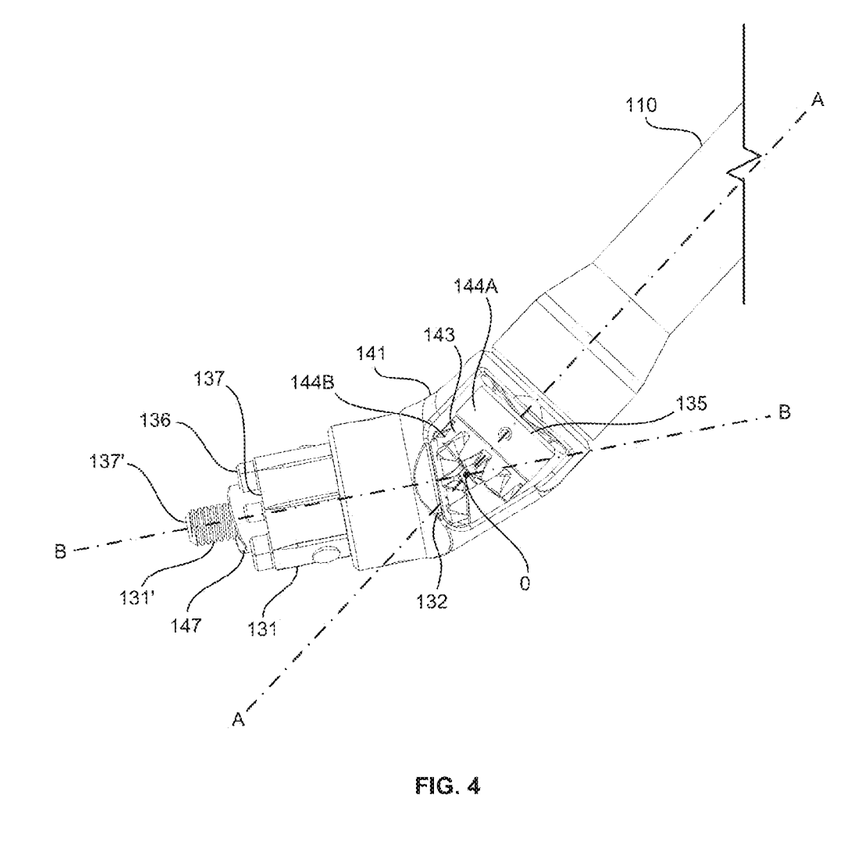
FIG. 4 is an enlarged view of the insertion end of the insertion tool shown in FIG. 1.

A first embodiment insertion tool 100 is depicted in FIG. 1. As shown, tool 100 comprises a tube 110 with a handle end 120, an inserter end 140 opposite handle end 120, an outer driveshaft 130 extending within a portion of tube 110, and an inner connecting shaft 130' extending concentrically within a part of driveshaft 130 (as best shown in FIG. 3). Inserter end 140 includes a curved portion 141 to permit insertion of an implant in the spine from a posterior approach. Notably, curved portion 141 is configured to allow insertion of an implant in a spine from a posterior approach without engaging the spinal cord. While curved portion 141 is shown as curvilinear, it should be noted that curved portion 141 may also be angular, segmented, or any combination thereof.

Figure 2:
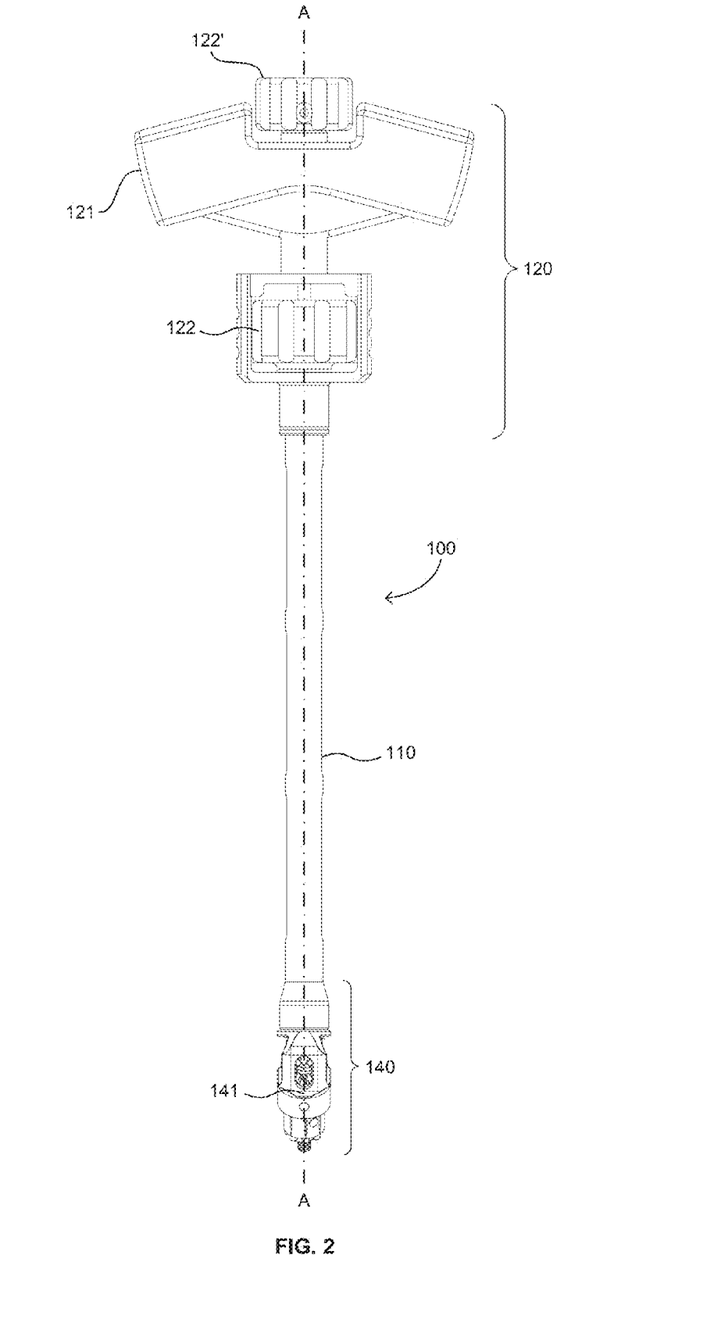
FIG. 2 is a left side view of the insertion tool shown in FIG. 1.

In addition to allowing for the grasping of tool 100 via grasping surface 121, handle end 120 includes components for translating a rotational force to either driveshaft 130 or connecting shaft 130'. As best depicted in FIG. 2, handle end 120 includes a knob 122 turnably attached to tube 110 and rigidly attached to driveshaft 130, and a knob 122' turnably attached to tube 110 and rigidly attached to connecting shaft 130'. Turning either knob 122 or 122' translates a rotational force to either driveshaft 130 or connecting shaft 130', respectively. Other variations of handle end 120 are also possible, of course, depending upon the configuration of insertion tool 100, as discussed below. It is contemplated that knobs 122, 122', driveshaft 130 and connecting shaft 130' can be configured so as to allow their disassembly from the remainder of tool 100. This may allow for the tool to be more easily sterilized. Of course, it is also contemplated to configure other components of the tool in such a modular fashion to serve the same goal.

FIG. 3 demonstrates that driveshaft 130 is rigid while connecting shaft 130' is flexible. Moreover, FIG. 3 further demonstrates that driveshaft 130 and connecting shaft 130' each have an operative end 133 or 133' proximate to knob 122 or 122', an actuator 131 or 131' proximate to inserter end 140, and an elongated portion 134 or 134' spanning therebetween. In this embodiment, each of the elongated portions 134 and 134' extend along longitudinal axis A-A within tube 110 into curved portion 141 of inserter end 140. To permit implantation of an implant in a spine along a posterior approach, tube 110 has a longitudinal axis A-A and inserter end 140 has a longitudinal axis B-B transverse with the first longitudinal axis. Longitudinal axes A-A and B-B intersect at a point O within curved portion 141. The angle of intersection between axes A-A and B-B is between fifteen (15) and sixty (60) degrees; although any angle equal to or less than ninety (90) degrees is contemplated, depending upon the implant. It is also contemplated to provide a tool in accordance with the present invention in which this angle of intersection is variable. The variability of the angle can be locked in position at a desired angle or free to rotate about an axis of rotation.

Each shaft has unique characteristics. For example, elongated portion 134' and actuator 131' of connecting shaft 130' are embodied within a single flexible element. Elongated portion 134' extends concentrically within driveshaft 130 along axes A-A and B-B until actuator 131' extends through an open end 142B of inserter end 140. Alternatively, elongated portion 134 and actuator 131 of driveshaft 130 may be two rigid elements. In this example, elongated portion 134 is substantially parallel with longitudinal axis A-A while actuator 131 is substantially parallel with longitudinal axis B-B. These two rigid elements are operatively coupled within curved portion 141 by a linkage 143. Linkage 143 is best shown in the enlarged views of FIGS. 4 and 5, although one skilled in the art would recognize that additional variations are possible. As shown, linkage 143 includes a first gear 144A formed or otherwise attached an interior end 135 of elongated portion 134 and a second gear 144B formed or otherwise attached to an interior end 132 of actuator 131. Moreover, FIG. 5 best shows that each of the first and second gears 144A and 144B has a respective center bore 145A and 145B to permit continuous passage of connecting shaft 130' therethrough. Although shown as flexible, this section of connecting shaft 130' may also be a universal joint, bearing joint, wire-wound like a spring to add flexible capability, manufactured from a series of material-removed sections to allow for flexibility, or any other equivalent structure.

Figure 5:
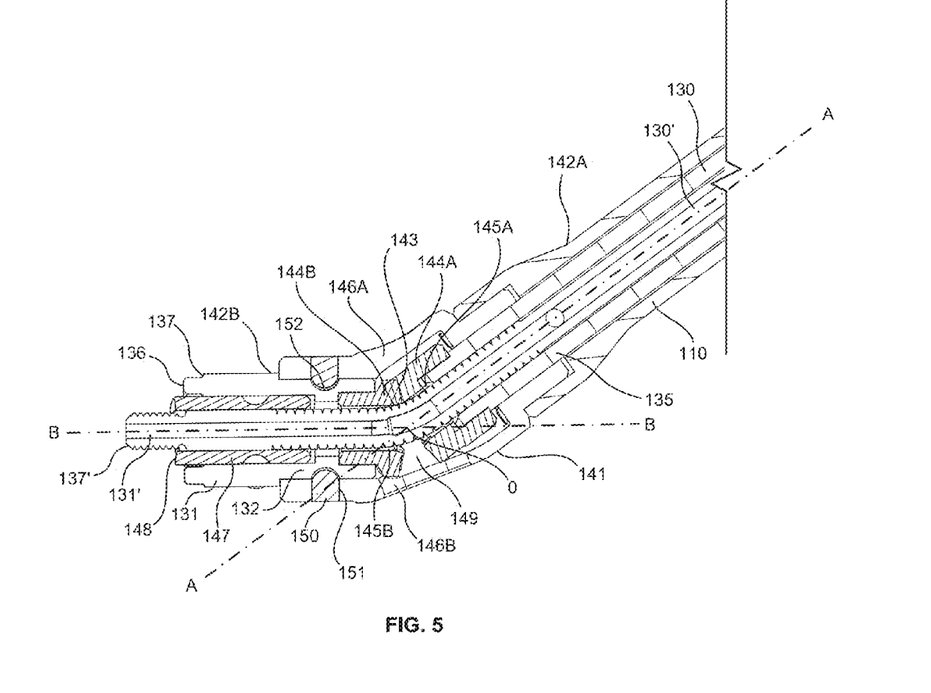
FIG. 5 is an enlarged cross-sectional view of the insertion end shown in FIG. 4.

FIG. 5 also shows that curved portion 141 has an open crescent shape formed by a first curved surface 146A opposite of a second curved surface 146B. Each of the first and second curved surfaces 146A and 146B spans between attached end 142A and open end 142B of inserter end 140. By virtue of this configuration, inserter end 140 engages first gear 144A with second gear 144B within curved portion 141. Moreover, a window 149 is advantageously created within curved portion 141. Window 149 may provide a number of important benefits, such as ease of assembly or weight reduction, as well as the ability to more easily sterilize the instrument. Although not shown in FIGS. 1-6, curved portion 141 may alternatively be sealed to prevent contaminants from entering tube 110. For example, curved portion 141 may be assembled from two portions that are affixed or welded together to form a sealed housing. Alternatively, each opening of curved portion 141 may have a sealing mechanism, such as a wax seal or O-ring.

The embodiment described above and depicted in FIGS. 1-5 permits driveshaft 130 and connecting shaft 130' to translate different degrees of rotational force to each of the respective actuators 131 and 131' for at least two reasons. First, driveshaft 130 has a dimensional advantage over connecting shaft 130' that permits driveshaft 130 to translate a greater degree of rotational force. For example, FIG. 5 shows that the outer radius of driveshaft 130 is larger than the outer radius of connecting shaft 130', otherwise the two driveshafts could not elongate concentrically. Therefore, driveshaft 130 may translate a higher degree of rotational force, even if driveshaft 130 and connecting shaft 130' are manufactured from the same material, because the strength of each driveshaft is relative to its outer radii. Second, because driveshaft 130 need not be flexible, it may be made from a higher-strength material (e.g., titanium) than the material used to make connecting shaft 130' (e.g., a flexible polymer); thus enabling driveshaft 130 to be inherently stronger.

By virtue of these advantages, actuators 131 and 131' may be employed for different purposes. The structure of each actuator is specific to their respective purposes. For example, actuator 131 is utilized to expand the implant, which requires a higher degree of rotational force. Therefore, actuator 131 includes a plurality of nubs 136 for engaging a corresponding expansion mechanism on the implant. As shown, nubs 136 are cylindrical and extend in a direction parallel to longitudinal axis B-B from a terminal face 137 of actuator 131. As another example, actuator 131' terminates in a threaded tip 137' for engaging a corresponding threaded bore formed in the implant. Because of these complimentary structures, rotation of threaded tip 137' both engages the implant with insertion tool 100 and aligns nubs 136 with the corresponding expansion structure on the implant. Once engaged, rotation of nubs 136 around axis B-B causes the implant to expand (discussed more fully below).

To ensure proper alignment of the implant with insertion tool 100, inserter end 140 has an alignment guide 147. As best shown in FIG. 5, alignment guide 147 extends along longitudinal axis B-B between actuators 131 and 131'. Preferably, alignment guide 147 has a mating surface 148 formed to match the exterior surface of the implant. For example, mating surface 148 is curved to match the curved surface of an implant. As a result, when the implant is attached to insertion tool 100 by rotation of threaded tip 137', alignment guide 147 causes the exterior surface of the implant to align with mating surface 148 and, thus, the corresponding expansion structure on the implant. Actuators 131 and 131' rotate independently of alignment guide 147, which does not rotate. For example, alignment guide 147 may be rotatably secured within actuator 131 by a screw 150 extending through a hole 151 in both inserter end 140 and actuator 131. To prevent alignment guide 147 from rotating with actuator 131, the bottom of screw 150 is received within a corresponding channel 152 on alignment guide 147, while the top of screw 149 remains flush with the interior surface of actuator 131.

In an alternate embodiment, an insertion tool similar to insertion tool 100 may include a flexible driveshaft and a flexible connecting shaft. This alternate tool may include an outer flexible driveshaft with an integral outer actuator and an inner flexible connecting shaft with an integral inner actuator. Like insertion tool 100, the inner flexible shaft may extend concentrically within the outer flexible shaft. In contrast to above, however, the use of an outer flexible driveshaft may permit the translation of rotational forces without the need for gears or the like. In such an embodiment, a lubricating agent, such as Teflon®, may be employed between the respective inner and outer shafts, or the alignment guide and the respective inner and outer actuators, to ensure that each element of the invention maintains rotational independence.

Figure 6:
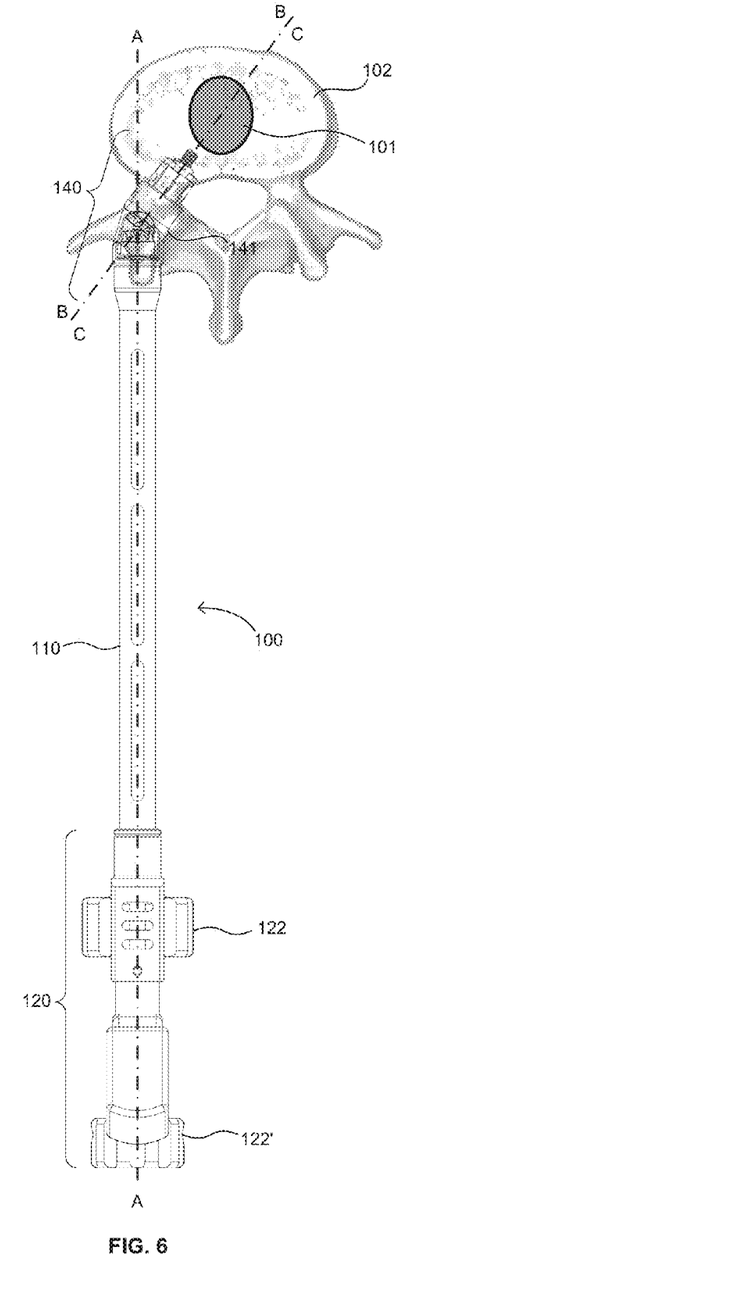
FIG. 6 is a top view of the insertion tool shown in FIG. 1 during insertion of an implant.

A method of using insertion tool 100 is now described with reference to FIG. 6, which features a top view of an insertion tool 100 in accordance with above. After an insertion area 102 is prepared according to the procedure being performed, an implant 101 is engaged with insertion tool 100. As discussed above, this step includes turning knob 122' to rotate actuator 131'. Thereby, advancing implant 101 towards mating surface 148 of alignment guide 147 along longitudinal axis B-B until nubs 136 engage a corresponding expansion mechanism (not shown) of implant 101.

Insertion tool 100 is configured to guide an implant 101 into the body along an axis C-C that is substantially parallel with longitudinal axis B-B. As shown in FIG. 6, axis C-C permits insertion of implant 101 in a spine from a posterior approach without engaging the spinal cord. Once implant 101 is positioned, knob 122 is turned in a first or second direction to adjust a dimension of the implant. The cooperation of nubs 136 with the corresponding expansion mechanism of implant 101 expands implant 101 to a desired height when knob 122 is turned. Depending upon the capabilities of implant 101, this expansion step may require the use of an additional distracter tool; however, certain implant designs may allow for distraction of vertebrae without the use of such extra tooling. Upon full expansion of the implant, knob 122' is turned oppositely to rotate actuator 131' in the opposite direction, thus disengaging implant 101 from insertion tool 100.

Figure 7:
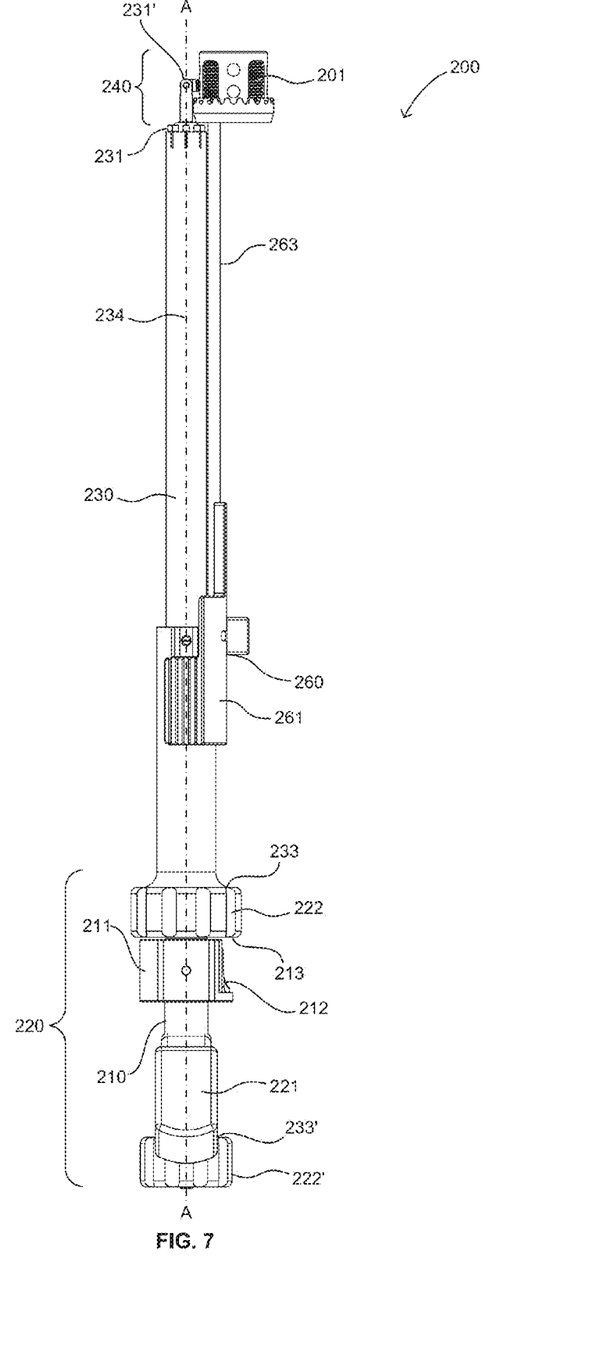
FIG. 7 is a perspective view of another embodiment of an insertion tool in accordance with the present invention.
Figure 8:
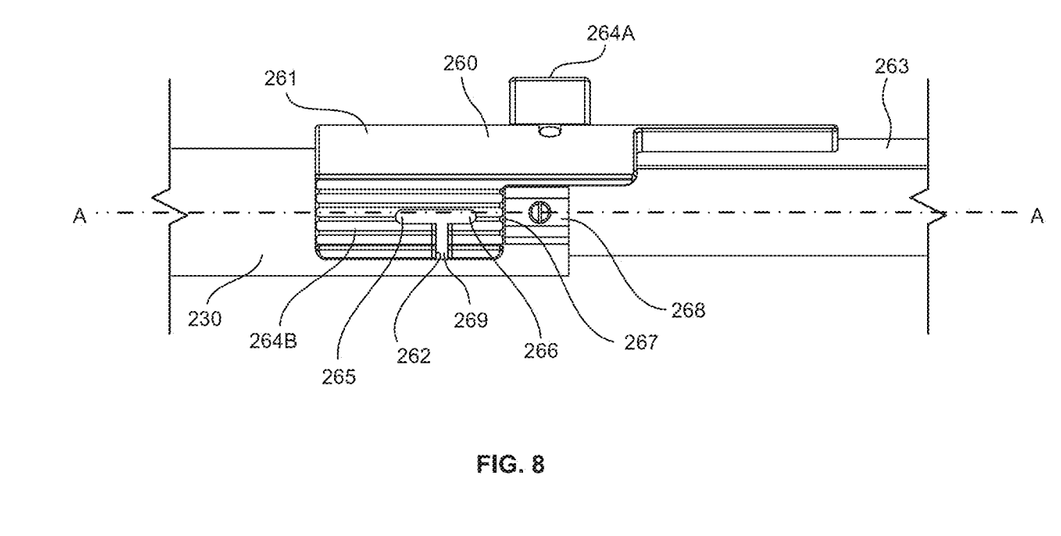
FIG. 8 is an enlarged view focusing on a portion of the slidelock of the insertion tool shown in FIG. 7.
Figure 9:
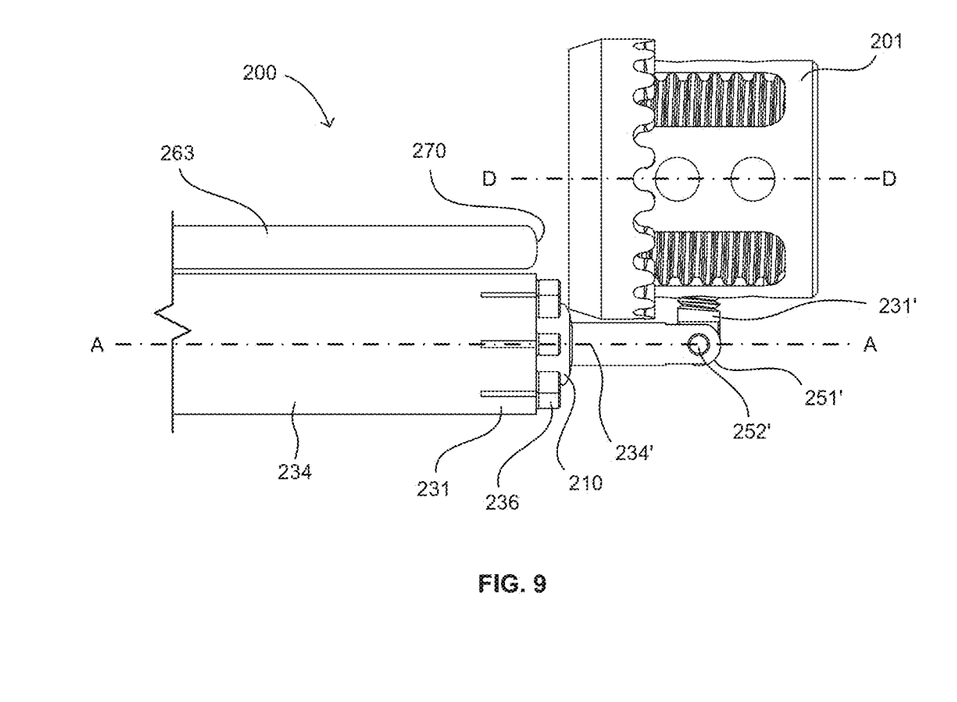
FIG. 9 is an enlarged view of the insertion end of the insertion tool shown in FIG. 7, with the slidelock disengaged with the implant.
Figure 10:
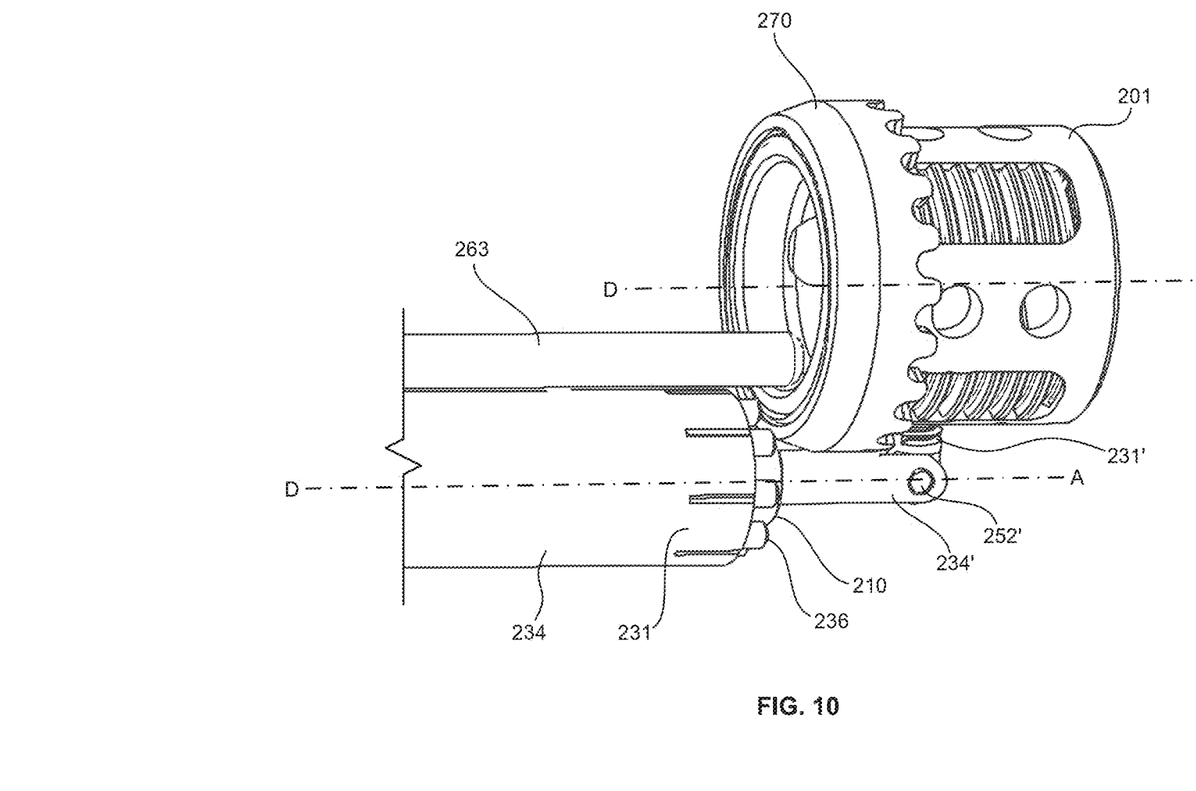
FIG. 10 is an enlarged view of the insertion end of the insertion tool shown in FIG. 7, with the slidelock engaged with the implant.

FIGS. 7-10 depict an alternate embodiment insertion tool 200. Where similar components to those of tool 100 are included in tool 200, similar reference numerals are utilized, but within the 200 series of numbers. For instance, insertion tool 200 similarly includes a tube 210 extending along a longitudinal axis A-A with a handle end 220 and an inserter end 240 opposite handle end 220. Insertion tool 200 also includes an outer driveshaft 230 and an inner connecting shaft 230' (the latter of which is best shown in FIGS. 9-10). In this embodiment, however, driveshaft 230 extends over tube 210 while connecting shaft 230' extends within tube 210.

As shown in FIG. 7, handle end 220 provides a grasping surface 221 and includes components for translating a rotational force to either driveshaft 230 or connecting shaft 230'. Handle end 220 includes a knob 222' that is turnably attached to tube 210 and rigidly attached to connecting shaft 230'. In contrast to above, however, tube 210 is sandwiched between driveshaft 230 and connecting shaft 230'. This advantageously permits knob 222 to be integral with a driveshaft 230 that is slidably and rotatably attached to the exterior surface of tube 210. Accordingly, turning knob 222 directly rotates driveshaft 230, and applying a sliding force to knob 222 advances driveshaft 230 along longitudinal axis A-A. Tube 210 has a retention mechanism 211 to prevent driveshaft 230 from either rotating or sliding when activated. Retention mechanism 211 includes a locking button 212 engageable with a receiving portion 213 of knob 222. For example, in FIG. 7, retention mechanism 211 is attached to a locking arm (not shown) while receiving portion 213 is a corresponding hook for receiving the arm (also not shown).

Each of driveshaft 230 and connecting shaft 230' has an operative end 233 or 233' proximate to a knob 222 or 222', an actuator 231 or 231' proximate to inserter end 240, and an elongated portion 234 or 234' spanning therebetween. FIG. 9 shows that actuator 231 has a plurality of nubs 236 similar in form and function to nubs 136. Elongated portion 234' and actuator 231' of connecting shaft 230' are distinct elements within tool 200. To connect these two elements, insertion tool 200 further includes a joint 251' for rotatably coupling elongated portion 234' with actuator 231'. Joint 251' is a hinge configured to receive a pin 252', although one skilled in the art would recognize that joint 251' may also be a bearing joint, universal joint, or equivalently bendable structure.

Actuator 231' of connecting shaft 230' also has a threaded tip 237' (not shown) for engaging implant 201 in substantially the same manner as threaded tip 137'. Because of joint 251', however, connecting shaft 230' can be bent relative to driveshaft 230. For example, connecting shaft 230' can be bent approximately ninety (90) degrees about an axis transverse with longitudinal axis A-A, as best shown in FIG. 9. Bending connecting shaft 230' advantageously permits implant 201 to be implanted within a smaller incision, even if it is a taller height implant. For example, if implant 201 is a taller height spinal implant, then it has a first dimension along the cranial-caudal axis of the spine that is greater than a second dimension along the ventral-dorsal axis. By bending joint 251' to rotate the cranial-caudal axis of implant 201 (shown as axis D-D) until it is substantially parallel with longitudinal axis A-A, the incision size may be defined by the smaller second dimension.

Joint 251' may be locked in a bent position. For example, FIGS. 7 and 8 depict a slidelock 260 mounted to the exterior of driveshaft 230. Slidelock 260 has an engagement portion 261, a locking mechanism 262, and a locking rod 263. Engagement portion 261 is proximate to operative end 233 and has a semi-circular portion with a first dimension. Driveshaft 230 has a circular cross-section that is smaller than that of engagement portion 261 to permit sliding along longitudinal axis A-A. Joint 251' is locked by sliding locking rod 263 into implant 201 (best shown in FIG. 10) and unlocked by sliding locking rod 263 in the opposite direction. Of course, engagement portion 261 may also be configured to slide along driveshaft 230 if their respective cross-sections are rectilinear, triangular, or any other shape.

FIG. 8 shows slidelock 260 in greater detail. For example, engagement portion 261 has a first block 264a and a gripping surface 264b, both of which may operate slidelock 260 by application of a sliding force thereto. Slidelock 260 operates within the boundary defined by locking mechanism 262. For example, locking mechanism 262 includes an elongated slot 265 on engagement portion 261 for receiving a post 266 attached to driveshaft 230. As another example, locking mechanism 262 also includes a flat edge 267 of engagement portion 261 abutting a second block 268 on the surface of driveshaft 230. Engagement portion 261 has a guiding channel 269 to ease assembly of insertion tool 200. Because of guiding channel 269, for example, engagement portion 261 may be slid over driveshaft 230 until post 266 is guided into elongated slot 265. Alternatively, engagement portion 261 may be snap fit over driveshaft 230 and the components of locking mechanism 262, thus permitting elongated slot 269 to be omitted.

FIGS. 7-10 also disclose an embodiment of locking rod 263. Locking rod 263 is attached to slidelock 260 and extends along longitudinal axis A-A until a terminal end 270 of locking rod 263 is proximate to implant 201. Advancing slidelock 260 thus advances locking rod 263 into implant 201 to lock joint 251' in a bent position.

A method of using insertion tool 200 is now discussed with reference to FIGS. 7-10. After the insertion area is prepared, knob 222' is turned to rotate actuator 231' in a first direction to engage tool 200 with implant 201. More particularly, rotating actuator 231' advances threaded tip 237' into a threaded bore (not shown) on implant 201. Once engaged, connecting shaft 230' is bent relative to driveshaft 230 via joint 251'. For example, as shown in FIG. 9, connecting shaft 230' may be bent approximately ninety (90) degrees via joint 251'. Preferably, bending connecting shaft 230' renders the cranial-caudal axis of implant 201 (axis D-D) substantially parallel with longitudinal axis A-A of tool 200. Slidelock 260 is then advanced in a first direction to lock joint 251' in a bent position as shown in FIG. 10. With joint 251' locked, implant 200 is inserted into the body. In some embodiments of tool 200, implant 201 may be inserted into a spine along an axis that is substantially parallel with the dorsal-ventral axis of the spine. Alternatively, implant 201 may be inserted along a longitudinal axis C-C that is substantially similar to axis C-C of FIG. 6, or any substantially equivalent angle.

After implant 201 has been inserted into the body, slide-lock 260 is advanced in a second direction, opposite of the first direction, to unlock joint 251' and permit implant 201 to freely return to its unrotated position. Preferably, implant 201 freely rotates until axis D-D is substantially parallel with the cranial-caudal axis of the spine. Driveshaft 230 is then slid over tube 210 along longitudinal axis A-A in the first direction until nubs 236 engage the corresponding expansion mechanism of implant 201. In some embodiments, sliding driveshaft 230 in a first direction may cause implant 201 to forcefully rotate into position if the confines of the insertion area preclude free rotation. Knob 222 is then turned in a first or second direction to adjust a dimension of the implant. As before, the cooperation of nubs 236 with implant 201 expands implant 201 to a desired height when knob 222 is turned. In some embodiments, this expansion step may require the use of an additional distracter tool. Once implant 201 has been expanded, knob 222' is turned oppositely to rotate actuator 231' in the opposite direction, thus disengaging implant 201 from tool 200.

While not shown in FIGS. 1-10, it should be further noted that elements of insertion tools 100 and 200 may be combined to form alternate embodiments based upon this disclosure. For example, an alternate tool may combine a curved portion, like curved portion 141, with the capabilities of joint 251' and slidelock 260; thereby permitting insertion of an implant in the spine from a posterior approach along axis C-C using a smaller incision. As another example, handle end 120 or 220 may be configured to receive a flexible driveshaft, like connecting shaft 230', with a joint 251' that is biased in a rotated position. In which case, the implant is rotated by retraction of the inner connecting shaft into the outer driveshaft or tube by application of a sliding force to a knob similar to knob 222'.

Although the invention disclosed in this application has been described with reference to particular embodiments, it is to be understood that these embodiments are merely illustrative of the principles and applications of the present invention. Accordingly, numerous modifications may be made to the illustrative embodiments, and other arrangements may be devised, without departing from the spirit and scope of the invention disclosed in this application.

The invention claimed is:

1. An implant insertion tool, comprising:
a tube with a handle end, an inserter end having an opening, and a curved portion located between the handle end and the inserter end;
a driveshaft with an actuator for actuating an implant, the driveshaft extending within the tube so that the actuator is proximate to the opening;
a connecting shaft extending within a portion of the driveshaft for connecting to the implant; and
a knob attached to the handle end and the driveshaft, wherein turning the knob rotates the actuator.

2. The implant insertion tool of claim 1, wherein the tube has a first longitudinal axis on a first side of the curved portion and a second longitudinal axis transverse with the first longitudinal axis on a second side of the curved portion.

3. The implant insertion tool of claim 1, wherein the driveshaft includes a first rigid portion and a second rigid portion, the first and second rigid portions being joined by a linkage in the curved portion.

4. The implant insertion tool of claim 3, wherein the connecting shaft extends continuously through the curved portion and includes a second actuator proximate to the first actuator.

5. The implant insertion tool of claim 4, wherein the knob further comprises a first knob associated with the driveshaft and a second knob associated with the connecting shaft.

6. The implant insertion tool of claim 5, wherein the first actuator includes a plurality of nubs and the second actuator includes a threaded tip.

7. A system comprising an expandable implant attached to the implant insertion tool of claim 6.

8. The implant insertion tool of claim 4, wherein the connecting shaft comprises a flexible material.

9. A system comprising an expandable implant attached to the implant insertion tool of claim 1.

10. An implant insertion tool, comprising:
a tube with a handle end and an inserter end opposite the handle end, the tube extending along a longitudinal axis;
a driveshaft with a first actuator and a first knob, the driveshaft extending over the tube so that the first actuator is proximate to an open end of the inserter end;
a connecting shaft with a second actuator, the connecting shaft extending within the tube so that the second actuator is proximate to the first actuator; and
a second knob turnably attached to the handle end and rigidly attached to the connecting shaft,
wherein, turning either the first or second knob rotates the respective first or second actuator for implantation of an expandable implant.

11. The implant insertion tool of claim 10, wherein the connecting shaft has a joint proximate to the open end for bending the connecting shaft relative to the driveshaft.

12. The implant insertion tool of claim 11, wherein a slidelock is slidably mounted to the driveshaft for locking the connecting shaft in a bent position.

13. The implant insertion tool of claim 12, wherein the driveshaft is operatively attached to a release on the tube, the release being configured to prevent the driveshaft from moving without actuation thereof.

* * * * *